(12) United States Patent
Bousquet et al.

(10) Patent No.: US 6,300,366 B1
(45) Date of Patent: Oct. 9, 2001

(54) AMINOPYRROLINE COMPOUNDS

(75) Inventors: Pascal Bousquet, Strasbourg; Jean-Daniel Ehrhardt, Kleinfrankenheim; Véronique Bruban, Strasbourg; Josiane Feldman, Strasbourg; Stephan Schann, Strasbourg; Elisabeth Scalbert, Paris; Bruno Pfeiffer, Saint Leu la Foret; Pierre Renard, Le Chesnay, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/714,090

(22) Filed: Nov. 16, 2000

(30) Foreign Application Priority Data

Nov. 17, 1999 (FR) .................................................. 99 14434

(51) Int. Cl.$^7$ ........................ A61K 31/40; A61K 31/403; C07D 209/02; C07D 207/22; A61N 9/02
(52) U.S. Cl. .......................... 514/426; 548/558; 548/559; 548/452; 514/412
(58) Field of Search .................................. 548/558, 559, 548/452; 514/426, 416

(56) References Cited

U.S. PATENT DOCUMENTS 3,887,569 * 6/1975 Poos et al. ...................... 260/293.78
4,016,175 * 4/1977 Schaafsma et al. ............. 260/326.62

OTHER PUBLICATIONS

Soon Ho Hwang, Arch. of Pharm. 331(4), pp. 139–142 (1998).*

* cited by examiner

Primary Examiner—Robert W. Ramsuer
Assistant Examiner—Kamal Saeed
(74) Attorney, Agent, or Firm—The Firm of Hueschen and Sage; G. Patrick Sage

(57) ABSTRACT

Compound of formula (I):

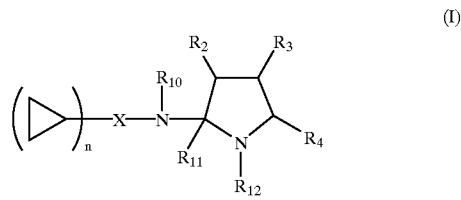

in which:

n is 1 or 2,

X represents alkylene, alkenylene, alkynylene or optionally substituted arylene or heteroarylene, $R_{10}$ represents hydrogen or alkyl and $R_{11}$ and $R_{12}$ together form a bond, or alternatively $R_{12}$ represents hydrogen or alkyl and $R_{10}$ and $R_{11}$ together form a bond, $R_2$, $R_3$ and $R_4$ each independently of the others represents hydrogen, alkyl, hydroxyalkyl, alkoxy, alkoxycarbonyl, aryl, arylalkyl or aryloxyalkyl, or two of $R_2$, $R_3$ and $R_4$ form a cycloalkyl radical.

Medicinal products containing the same are useful in the treatment of cardiovascular diseases.

15 Claims, No Drawings

AMINOPYRROLINE COMPOUNDS

DESCRIPTION OF THE PRIOR ART

Compounds having a 2-aminopyrroline structure have been described for their anti-diarrhoal (EP 0155653) or antiparasitic (DE 2029297) properties.

BACKGROUND OF THE INVENTION

The compounds of the present invention have a novel structure which is characterised by the presence of a cyclopropyl group associated with the aminopyrroline ring. That structure gives them valuable pharmacological properties. In particular, tests have shown them to be capable of inducing a fall in cardiac frequency, as well as in disorders of cardiac rhythm. Accordingly, the compounds of the invention are used in the treatment of cardiovascular diseases, especially arterial hypertension, arrhythmia and associated disorders.

DETAILED DESCRIPTION OF THE INVENTION

The present invention relates to compounds of formula (I):

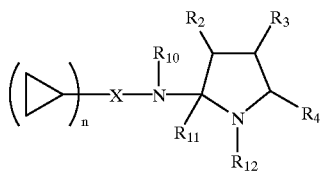

in which:
  n is 1 or 2,
  X represents an alkylene, alkenylene or alkynylene group, or an optionally substituted arylene group, or an optionally substituted heteroarylene group,
  $R_{10}$ represents a hydrogen atom or a linear or branched ($C_1$–$C_6$)alkyl group and $R_{11}$, and $R_{12}$ together form a bond, or alternatively $R_{12}$ represents a hydrogen atom or a linear or branched ($C_1$–$C_6$)alkyl group and $R_{10}$ and $R_{11}$ together form a bond,
  $R_2$, $R_3$ and $R_4$ each independently of the others represents; a hydrogen atom, a linear or branched ($C_1$–$C_6$)alkyl group, a linear or branched ($C_1$–$C_6$)hydroxyalkyl group, a linear or branched ($C_1$–$C_6$)alkoxy group, a linear or branched ($C_1$–$C_6$)alkoxycarbonyl group, an optionally substituted aryl group, an optionally substituted arylalkyl group in which the alkyl moiety is linear or branched and has from 1 to 6 carbon atoms, or an optionally substituted aryloxyalkyl group in which the alkyl moiety is linear or branched and has from 1 to 6 carbon atoms, or alternatively two of $R_2$, $R_3$ and $R_4$, with the carbon atoms carrying them, form a ($C_5$–$C_7$) cycloalkyl group,
wherein:
  the term alkylene denotes a linear or branched divalent group containing from 1 to 6 carbon atoms,
  the term alkenylene denotes a linear or branched divalent group containing from 2 to 6 carbon atoms and from 1 to 3 double bonds,
  the term alkynylene denotes a linear or branched divalent group containing from 2 to 6 carbon atoms and from 1 to 3 triple bonds,
  the term aryl represents a phenyl or naphthyl group, and the term arylene represents a divalent group of the same type,
  the term heteroaryl denotes a mono- or bi-cyclic unsaturated or partially unsaturated group having from 4 to 11 ring members and from 1 to 5 hetero atoms selected from nitrogen, oxygen and sulphur, and the term heteroarylene represents a divalent group of the same type,
  the term substituted associated with the expressions cryl, arylene, arylalkyl, aryloxyalkyl, heteroaryl and heteroarylene means that the groups in question are substituted in the aromatic moiety by one or more groups selected from halogen atoms or linear or branched ($C_1$–$C_6$)alkyl groups, linear or branched ($C_1$–$C_6$)alkoxy groups, hydroxy groups, cyano groups, nitro groups or amino groups (optionally substituted by one or two linear or branched ($C_1$–$C_6$) alkyl groups),
their enantiomers and diastereoisomers, and addition salts thereof with a pharmaceutically acceptable acid or base.

An advantageous aspect of the invention relates to compounds in which X represents an optionally substituted arylene group or an optionally substituted heteroarylene group. Of those compounds, very special preference will be given to those in which X represents an optionally substituted arylene group, for example a phenylene group.

Another advantageous aspect of the invention relates to compounds in which X represents an alkylene, alkenylene or alkynylene group, more especially an alkylene group.

Preferred compounds of the invention are those in which $R_{11}$ and $R_{12}$ together form a bond, $R_{10}$ preferably being a hydrogen atom.

Other preferred compounds of the invention are those in which each of $R_2$, $R_3$ and $R_4$ represents a hydrogen atom.

An especially advantageous aspect of the invention relates to compounds of formula (I) in which X represents an alkylene group or an optionally substituted arylene group, $R_{10}$ represents a hydrogen atom or a linear or branched ($C_1$–$C_6$)alkyl group, $R_{11}$ and $R_{12}$ together form a bond, and $R_2$, $R_3$ and $R_4$ each independently of the others represents a hydrogen atom, a linear or branched ($C_1$–$C_6$)alkyl group, a linear or branched ($C_1$–$C_6$)-hydroxyalkyl group, a linear or branched ($C_1$–$C_6$)alkoxycarbonyl group, a linear or branched ($C_1$–$C_6$)alkoxy group, an optionally substituted aryl group, or an optionally substituted aryloxyalkyl group in which the alkyl moiety is linear or branched and has from 1 to 6 carbon atoms.

The preferred arylene group of the invention is the phenylene group.

Of the preferred compounds of the invention, special mention may be made of:
  N-(2-cyclopropylphenyl)-3,4-dihydro-2H-pyrrol-5-amine, and addition salts thereof with a pharmaceutically acceptable acid,
  N-(dicyclopropymethyl)-3,4-dihydro-2H-pyrrol-5-amine, and addition salts thereof with a pharmaceutically acceptable acid,
  N-(2-Cyclopropylphenyl)-2-methyl-3,4-dihydro-2H-pyrrol-5-amine, and addition salts thereof with a pharmaceutically acceptable acid.

The invention relates also to a process for the preparation of compounds of formula (I), which process is characterised in that there is used as starting material a compound of formula (II):

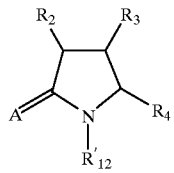

(II)

in which $R_2$, $R_3$ and $R_4$ are as defined in formula (I), $R'_{12}$ represents a hydrogen atom or a linear or branched $(C_1-C_6)$alkyl group, and A represents an oxygen atom or a sulphur atom, which is reacted:

either with an aromatic amine of formula (III):

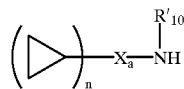

(III)

in which n is as defined in formula (I), $X_a$ represents an arylene or heteroarylene group, and $R'_{10}$ represents a hydrogen atom or a linear or branched $(C_1-C_6)$alkyl group, to yield a compound of formula (I/a):

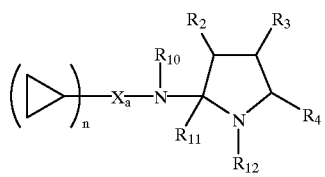

(I/a)

a particular case of the compounds of formula (I) in which $R_2$, $R_3$, $R_4$ and n are as defined above, $X_a$ represents an arylene or heteroarylene group, and $R_{10}$, $R_{11}$ and $R_{12}$ are as defined in formula (I), or with a methylating agent, such as, for example dimethyl sulphate or methyl iodide, to yield, after treatment in a basic medium, an intermediate which is treated directly in an alcoholic medium with an amine hydrochloride (IV):

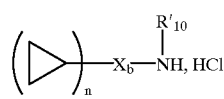

(IV)

in which $R_1$ and n are as defined in formula (I), $X_b$ represents an alkylene, alkenylene or alkynylene group, and $R'_{10}$ represents a hydrogen atom or a linear or branched $(C_1-C_6)$alkyl group, to yield a compound of formula (I/b):

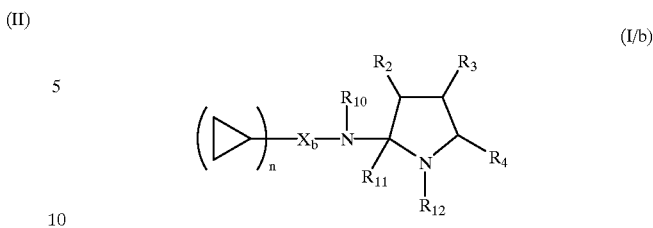

(I/b)

a particular case of the compounds of formula (I) in which $R_1$, $R_2$, $R_3$, $R_4$ and n are as defined above and $X_b$ represents an alkylene, alkenylene or alkynylene group, which compounds (I/a) and (I/b) form the totality of the compounds of formula (I), and:
 which may, where appropriate, be purified according to a conventional purification technique,
 which are separated, where appropriate, into their stereoisomers according to a conventional separation technique,
 which are converted, if desired, into their addition salts with a pharmaceutically acceptable acid or base.

The present invention relates also to pharmaceutical compositions comprising as active ingredient at least one compound of formula (I) alone or in combination with one or more inert, non-toxic, pharmaceutically acceptable excipients or carriers.

Of the pharmaceutical compositions according to the invention, special mention may be made of those which are suitable for oral, parenteral and nasal administration, tablets, dragees, sublingual tablets, gelatin capsules, lozenges, suppositories, creams, ointments, dermal gels, etc.

The dosage used varies according to the age and weight of the patient, the nature and severity of the disorder, and the route of administration, which may be oral, nasal, rectal or parenteral. In general, the unit dose ranges from 0.1 to 500 ml for a treatment in from 1 to 3 doses per 24 hours.

The Examples which follow illustrate the invention and do not limit it in any way.

The starting materials used are products which are known or prepared according to known methods.

PREPARATION A

2-Cyclopropylaniline

A solution of 5 g (42 mmol) of cyclopropylbenzene in 20 ml of acetic anhydride is cooled to 15° C. While keeping the temperature below 20° C., 3.7 ml of 68% nitric acid are added slowly. The reaction mixture is stirred for one hour at that temperature, hydrolysed, rendered alkaline with 2N sodium hydroxide solution and extracted twice with 100 ml of ether. The organic phase is then dried and concentrated to yield a mixture of 2-nitrocyclo-propylbenzene and 4-nitrocyclopropylbenzene. The mixture is dissolved in 15 ml of ethanol and hydrogenated at normal temperature and pressure in the presence of 50 mg of $PtO_2$. The residue obtained after filtering off the catalyst and evaporating off the solvent is purified by chromatography on silica gel to yield the title product.

PREPARATION B

4-Cyclopropylaniline

The expected product is obtained in the course of the synthesis of the compound described in Preparation A.

PREPARATION C

2-Chloro-4-cyclopropylaniline

A solution of 7.9 mmol (1.05 g) of 4-cyclopropylaniline (Preparation B) in 15 ml of acetic anhydride is stirred for 3 hours at ambient temperature. The reaction mixture is concentrated. The residue is taken up in water, neutralised and extracted twice with dichloromethane.

The organic phase is dried and concentrated. The 4-cyclopropylacetanilide is dissolved in acetic acid and treated with 10 mmol of chlorine. After 30 minutes, the solvent is evaporated off and the resulting residue is taken up in 100 ml of ethanol and then hydrolysed with potassium hydroxide at reflux. The ethanol is then evaporated off, and the residue is taken up in water and extracted twice with dichloromethane. The organic phase is then dried and concentrated, and the resulting residue is purified by chromatography on silica gel to yield the title product.

PREPARATION D

4-Chloro-2-cyclopropylaniline

The expected product is obtained according to the process described in Preparation C, using the compound described in Preparation A as starting material.

PREPARATION E

2,4-Dicyclopropylaniline

The expected product is obtained according to the process described in Preparation A, starting from m-dicyclopropylbenzene, the preparation of which is described in Chem. Ber., 1973, 106, 511–524.

PREPARATION F

2,5-Dicyclopropylaniline

The expected product is obtained according to the process described in Preparation A, starting from p-dicyclopropylbenzene, the preparation of which is described in Chem. Ber., 1973, 106, 511–524.

PREPARATION G

3,4-Dicyclopropylaniline

The expected product is obtained according to the process described in Preparation A, starting from o-dicyclopropylbenzene, the preparation of which is described in Chem. Ber., 1973, 106, 511–524.

EXAMPLE 1

N-(2-Cyclopropylphenyl)-3,4-dihydro-2H-pyrrol-5-amine hydrochloride 5 mmol (425 mg) of 2-pyrrolidinone and 5 mmol (766 mg) of phosphorus oxychloride are added to a solution of 5 mmol (666 mg) of 2-cyclopropylaniline in 30 ml of 1,2-dichloroethane. The whole is heated at 60° C. for 3.5 hours. After evaporation of the solvent, the residue is taken up in water, rendered alkaline with the aid of sodium carbonate, and extracted twice with 100 ml of ether. The organic phase is then dried, concentrated and purified by chromatography on silica gel to yield the expected product. The corresponding hydrochloride is obtained by the action of a titrated solution of hydrochloric acid in ethanol.

Melting point: 182–184° C.

EXAMPLE 2

N-(4-Chloro-2-cyclopropylphenyl)-3,4-dihydro-2H-pyrrol-5-amine hydrochloride The expected product is obtained according to the process described in Example 1, using the compound described in Preparation D as starting material.

Melting point: 198–199° C.

EXAMPLE 3

N-(4-Cyclopropylphenyl)-3,4-dihydro-2H-pyrrol-5-amine hydrochloride

The expected product is obtained according to the process described in Example 1, using the compound described in Preparation B as starting material.

EXAMPLE 4: N-(2-Chloro-4-cyclopropylphenyl)-3,4-dihydro-2H-pyrrol-5-amine hydrochloride The expected product is obtained according to the process d-scribed in Example 1, using the compound described in Preparation C as starting material.

Melting point: 149–151 ° C.

EXAMPLE 5

N-(Dicyclopropymethyl)-3,4-dihydro-2H-pyrrol-5-amine hydrochloride

A mixture of 0.2 mol (25.2 g) of dimethyl sulphate and 0.2 mol (17 g) of 2-pyrrolidinone is heated at 60° C. overnight. The reaction mixture is poured into a saturated iced $K_2CO_3$ solution. The aqueous phase is extracted twice with ether, and the combined organic phases are dried and concentrated. The residue is then distilled under reduced pressure. 2 mrnmol of the resulting product are dissolved in 20 ml of methanol, and 2 mmol (295 mg) of dicyclopropylmethylamine hydrochloride are added. The reaction mixture is stirred at 50° C. for 2 hours. After evaporation of the methanol, the residue is taken up in water, rendered alkaline and extracted twice with ether. The organic phase is dried, concentrated and purified to yield the expected product. The corresponding, hydrochloride is obtained by the action of a titrated solution of hydrochloric acid in ethanol.

Melting,point: 223–225° C.

EXAMPLE 6

N-(Dicyclopropymethyl)-3-methyl-3,4-dlihydro-2H-pyrrol-5-amine hydrochloride The expected product is obtained according to the process described in Example 5, by replacing 2-pyrrolidinone by 4-methyl-2-pyrrolidinone.

Melting point: 198–199° C.

EXAMPLE 7

N-(Dicyclopropymethyl)-2-methyl-3,4-clihydro-2H-pyrrol-5-amine hydrochloride The expected product is obtained according to the process described in Example 5, by replacing 2-pyrrolidinone by 5-methyl-2-pyrrolidinone.

Melting point: 144–146° C.

EXAMPLE 8

N-(Dicyclopropymethyl)-4-methyl-3,4-clihydro-2H-pyrrol-5-amine hydrochloride The expected product is obtained according to the process described in Example 5, by replacing 2-pyrrolidinone by 3-methyl-2-pyrrolidinone.

Melting point: 201–203° C.

EXAMPLE 9

N-(Dicyclopropymethyl)-2,3-dimethyl-3,4-dihydro-2H-pyrrol-5-amine hydrochloride The expected product is obtained according to the process described in Example 5, by replacing 2-pyrrolidinone by 4,5-dimethyl-2-pyrrolidinone.

Melting point: 143–145° C.

EXAMPLE 10

(cis)-N-(Dicyclopropylmethyl)-2,3-dimethyl-3,4-dihydro-2H-pyrrol-5-amine hydrochloride The expected product is obtained according to the process described in Example 5, by replacing 2-pyrrolidinone by (cis)-4,5-dimethyl-2-pyrrolidinotie.

Melting point: 163–165° C.

EXAMPLE 11

(trans)-N-(Dicyclopropylmethyl-2,3-dimiethyl-3,4-dihydro-2H-pyrrol-5-amine hydrochloride The expected product is obtained according to the process described in Example 5, by replacing 2-pyrrolidinone by (trans)-4,5-dimethyl-2-pyrrolidinone.

Melting point: 138–140° C.

EXAMPLE 12

N-(Dicyclopropylmethyl)-2-ethyl-3,4-dihydro-2H-pyrrol-5-amine hydrochloride

The expected product is obtained according to the process described in Example 5, by replacing 2-pyrrolidinone by 5-ethyl-2-pyrrolidinone.

Melting point: 108–1 1 0C.

EXAMPLE 13

3-(4-Chlorophenyl)-N-(dicyclopropylmethyl)-3,4-dihydro-2H-pyrrol-5-amine hydrochloride The expected product is obtained according to the process described in Example 5, by replacing 2-pyrrolidinone by 4-(4-chlorophenyl)-2-pyrrolidinone.

Meltine point: 220–223° C.

EXAMPLE 14

N-(Dicyclopropylmethyl)-3-[(2-methylphenoxy)methyl]-3,4-dihydro-2H-pyrrol-5-amine hydrochloride The expected product is obtained according to the process described in Example 5, by replacing 2-pyrrolidinone by 4-[(2-methylphenoxy)methyl]-2-pyrrolidinone.

Melting point: 193–194° C.

EXAMPLE 15

(cis)-N-(Dicyclopropylmethyl)-3a,4,5,6,7,7a-hexahydro-3H-indol-2-amine hydrochloride The expected product is obtained according to the process described in Example 5, by replacing 2-pyrrolidinone by (cis)-octahydro-2H-indol-8-one.

Melting point: 204–206° C.

EXAMPLE 16

N-(Dicyclopropylmethyl)-4-hydroxymet.hyl-3,4-dihydro-2H-pyrrol-5-amine hydrochloride 70 mmol of methyl iodide are added to 10 mmol of 4-hydroxymethylpyrrolidine-thione (the preparation of which is described in Tet. Lett., 1982, 23, 2947–2950) in solution in isopropanol. After stirring at ambient temperature, the solvent is evaporated off and then ethanol and dicyclopropylmethylamine (15 mmol) are added. After refluxing for 24 hours, the solvent is evaporated off and then the residue is taken up in water, rendered alkaline and then extracted with dichloromethane. After washing, drying and evaporation of the organic phase, the expected product is obtained in the form of a white solid. The corresponding hydrochloride is obtained by the action of a titrated solution of hydrochloric acid in ethanol.

Melting point: 199–200° C.

EXAMPLE 17

N-(Dicyclopropylmethyl)-4-methoxycarbonyl-3,4-dihydro-2H-pyrrol-5-amine hydrochloride The expected product is obtained according to the process described in Example 16, starting from 4-methoxycarbonylpyrrolidine-thione (the preparation of which is described in Tet. Lett., 1982, 23, 2947–2950).

Melting point: 123–125° C.

EXAMPLE 18

N-(2,4-Dicyclopropylphenyl)-3,4-dihydro-2H-pyrrol-5-amine hydrochloride

The expected product is obtained according to the process des;cribed in Example 1, starting from the compound described in Preparation E.

Melting point: 163–165° C.

EXAMPLE 19

N-(2,5-Dicyclopropylphenyl)-3,4-dihydro-2H-pyrrol-5-amine fumarate

The expected product is obtained according to the process described in Example 1, starting from the compound described in Preparation F. The fumarate is obtained by the action of a titrated solution of fumaric acid in ethanol.

Melting point: 174–176° C.

EXAMPLE 20

N-(3,4-Dicyclopropylphenyl)-3,4-dihydro-2H-pyrrol-5-amine fumarate

The expected product is obtained according to the process described in Example 19, starting from the compound described in Preparation G.

Melting point: 202–204° C.

EXAMPLE 21

N-(2-Cyclopropylphenyl)-2-methyl-3,4-dihydro-2H-pyrrol-5-amine hydrochloride

The expected product is obtained according to the process described in Example 1, starting from 5-methyl-2-pyrrolidinone.

Melting point: 138–139° C.

PHARMACOLOGICAL STUDY

EXAMPLE A

Demonstration of Antihypertensive Activity in Anaesthetised Normotensive Rabbits The experiments are carried out on normotensive male rabbits. The animals are anaesthetised with sodium pentobarbital (40 mg/kg) via the marginal vein of the ear. The rabbit is tracheotomised and immediately ventilated to the ambient air with the aid of a respirator. It is then curarised, and the right femoral vein and artery are catheterised.

Before each experiment, an equal volume of vehicle is administered and the parameters to be measured are allowed to stabilise for 15 to 25 minutes.

The test compounds or the vehicle are administered by the intracisternal (i.e.) or intravenous (i.v.) route. The arterial pressure (AP) is recorded. continuously by means of a catheter placed in the abdominal aorta via the right femoral artery and connected to a pressure sensor. The results are expressed in mmHg. Measurement of the cardiac frequency (CF) expressed in beats per minute (bpm) is carried out by rapid running of the recording of AP and counting over six seconds of recording.

The compounds of the invention appear to induce a fall in arterial pressure and bradycardia which are long-lasting.

By way of example, the results obtained with the compound of Example 1 are summarised in the following table:

| Compound of Example 1 Dose (mg/kg) | AP before injection (mmHg) | AP after injection (mmHg) | CF before injection (bpm) | CF after injection (bpm) |
| --- | --- | --- | --- | --- |
| 1 (i.v.) | 84 | 63 | 306 | 236 |
| 0.3 (i.v.) | 92 | 74 | 300 | 263 |
| 0.03 (i.c.) | 90 | 63 | 307 | 240 |

EXAMPLE B

Demonstration of Antihypertensive Activity in SHR

The experiments are carried out on spontaneously hypertensive rats (SHR). The animals are anaesthetised with pentobarbital by the intraperitoneal route (45 mg/kg). The femoral veins and arteries are catheterised for the administration of the test compounds. The animals are curarised and ventilated to the ambient air with the aid of a respirator.

Before each experiment, an equal volume of vehicle is administered and the parameters to be measured are allowed to stabilise for 15 to 25 minutes.

The test compounds or the vehicle are administered by the intracisternal (i.e.) or intravenous (i.v.) route. The arterial pressure (AP) is recorded continuously by means of a catheter placed in the abdominal aorta via the right femoral artery and connected to a pressure sensor. The results are expressed in mmHg. Measurement of the cardiac frequency (CF) expressed in beats per minute (bpm) is carried out by rapid running of the recording of AP and counting over six seconds of recording.

The compounds of the invention appear to induce hypotension and long-lasting bradycardia.

By way of example, the results obtained with the compounds of Example 1 and Example 21 are summarised in the following table:

| Example | Dose (mg/kg) | AP before injection (mmHg) | AP after injection (mmHg) | CF before injection (bpm) | CF after injection (bpm) |
| --- | --- | --- | --- | --- | --- |
| 1 | 1 (i.v.) | 163 | 91 | 386 | 296 |
| 21 | 10 (i.v.) | 166 | 138 | 375 | 320 |
| 21 | 0.1 (i.c.) | 134 | 99 | 345 | 320 |

Furthermore, the compound of Example 21 has no vasoconstrictor effect, whatever the

EXAMPLE C

Demonstration of Antiarrhythmic Activity in Anaesthetised Normotensive Rabbits

The experiments are carried out on normotensive male rabbits. The animals are anaesthetised with sodium pentobarbital (40 mg/kg) via the marginal vein of the ear. The rabbit is tracheotomised and immediately ventilated to the ambient air with the aid of a respirator. It is then curarised, and the right femoral vein and aurtery are catheterised.

The electrocardiogram is recorded by transcutaneous electrodes.

The compounds or the vehicle, then bicuculline (10 µ/kg), are administered by the interacisternal (i.c.) route.

The electrocardiogram is then recorded continuously for 30 minutes in order to count disturbances in rhythm.

The results are expressed as the number of ventricular extrasystoles (VES).

The compounds of the invention appear to induce a fall in the number of VES.

By way of example, the results obtained with the compound of Example 9 are summarised in the following table:

| | Number of animals in group | Average number of VES | Number of rabbits protected | % protection against disturbances in rhythm |
| --- | --- | --- | --- | --- |
| Control bicuculline | n = 8 | 1043 | 0 | 0 |
| Compound of Example 9 0.3 mg/kg i.c. route | n = 8 | 84 | 7 | 87.5 |

EXAMPLE D

Pharmaceutical Composition

Preparation formula for 1000 tablets each containing 10 mg:

compound of Example 1 ... 10 g
hydroxypropylcellulose ... 2 g
corn starch ... 10g
lactose ... 100 g
magnesium stearate ... 3 g
talc ... 3 g

We claim:

1. A compound selected from those of formula (1):

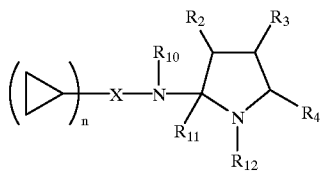

(I)

in which:
n is 1 or 2,
X represents alkylene, alkenylene or alkynylene, optionally substituted arylene, or optionally substituted heteroarylene,
$R_{10}$ represents hydrogen or a linear or branched ($C_1$–$C_6$) alkyl and $R_{11}$, and $R_{12}$ together form a bond, or alternatively $R_{12}$ represents hydrogen or linear or branched ($C_1$–$C_6$)alkyl and $R_{10}$ and $R_{11}$ together form a bond,
$R_2$, $R_3$ and $R_4$ each independently of the others represents hydrogen, linear or branched ($C_1$–$C_6$)alkyl, linear or branched ($C_1$–$C_6$)hydroxyalkyl, linear or branched ($C_1$–$C_6$)alkoxy, linear or branched ($C_1$–$C_6$) alkoxycarbonyl, optionally substituted aryl, optionally substituted arylalkyl in which the alkyl moiety is linear or branched and has from 1 to 6 carbon atoms, or optionally substituted aryloxyalkyl in which the alkyl moiety is linear or branched and has from 1 to 6 carbon atoms, or alternatively two of $R_2$, $R_3$ and $R_4$, with the carbon atoms carrying them, form a ($C_5$–$C_7$)cycloalkyl group, wherein:
the term alkylene denotes a linear or branched divalent group containing from 1 to 6 carbon atoms,
the term alkenylene denotes a linear or branched divalent group containing from 2 to 6 carbon atoms and from 1 to 3 double bonds,
the term alkynylene denotes a linear or branched divalent group containing from 2 to 6 carbon atoms and from 1 to 3 triple bonds,
the term aryl represents phenyl or naphthyl, and the term arylene represents a divalent group of the same type,
the term heteroaryl denotes a mono- or bi-cyclic unsaturated or partially unsaturated group having from 4 to 11 ring members and from 1 to 5 hetero atoms selected from nitrogen, oxygen and sulphur, and the term heteroarylene represents a divalent group of the same type,
the term substituted associated with the expressions aryl, arylene, arylalkyl, aryloxy-alkyl, heteroaryl and heteroarylene means that the groups in question are substituted in the aromatic moiety by one or more groups selected from halogen, linear or branched ($C_1$–$C_6$)alkyl, linear or branched ($C_1$–$C_6$)alkoxy, hydroxy, cyano, nitro or amino (optionally substituted by one or two linear or branched ($C_1$–$C_6$) alkyl),
its enantiomers and diastereoisomers, and addition salts thereof with a pharmaceutically acceptable acid or base.

2. A compound of claim 1 in which X represents optionally substituted arylene or optionally substituted heteroarylene.

3. A compound of claim 1 in which X represents alkylene, alkenylene or alkynylene.

4. A compound of claim 1 in which $R_{11}$ and $R_{12}$ together form a bond.

5. A compound of claim 1 in which each of $R_2$, $R_3$ and $R_4$ represents hydrogen.

6. A compound of claim 1 in which X represents alkylene or optionally substituted arylene, $R_{10}$ represents hydrogen or linear or branched ($C_1$–$C_6$)alkyl, $R_{11}$, and $R_{12}$ together form a bond, and $R_2$, $R_3$ and $R_4$ each independently of the others represents hydrogen, linear or branched ($C_1$–$C_6$)alkyl, linear or branched ($C_1$–$C_6$)hydroxyalkyl, linear or branched ($C_1$–$C_6$)alkoxycarbonyl, linear or branched ($C_1$–$C_6$)alkoxy, optionally substituted aryl, or optionally substituted aryloxyalkyl in which the alkyl moiety is linear or branched and has from 1 to 6 carbon atoms.

7. A compound of claim 1 which is N-(2-cyclopropylphenyl)-3,4-dihydro-2H-pyrrol-5-amine, and addition salts thereof with a pharmaceutically acceptable acid.

8. A compound of claim 1 which is N-(dicyclopropylmethyl)-3,4-dihydro-2H-pyrrol-5-amine, and addition salts thereof with a pharmaceutically acceptable acid.

9. A compound of claim 1 which is N-(2-Cyclopropylpheryl)-2-methyl-3,4-dihydro-2H-pyrrol-5-amine, and addition salts thereof with a pharmaceutically acceptable acid.

10. A method for treating an animal or human living body afflicted with a cardiovascular disease comprising the step of administering to the living body an amount of a compound of claim 1 which is effective for alleviation of said disease.

11. A method of claim 10 wherein the cardiovascular disease is arterial hypertension.

12. A method of claim 10 wherein the cardiovascular disease is arrhythmia.

13. A pharmaceutical composition useful in treating a cardiovascular disease comprising as active principle an effective amount of a compound as claimed in claim 1, together with one or more pharmaceutically acceptable excipients or vehicles.

14. A pharmaceutical composition useful in treating arterial hypertension comprising as active principle an effective amount of a compound as claimed in claim 1, together with one or more pharmaceutically acceptable excipients or vehicles.

15. A pharmaceutical composition useful in treating arrhythmia comprising as active principle an effective amount of a compound as claimed in claim 1, together with one or more pharmaceutically acceptable excipients or vehicles.

* * * * *

UNITED STATES PATENT AND TRADEMARK OFFICE
CERTIFICATE OF CORRECTION

PATENT NO. : 6,300,366 B1  Page 1 of 1
DATED : October 9, 2001
INVENTOR(S) : Pascal Bousquet et al.

It is certified that error appears in the above-identified patent and that said Letters Patent is hereby corrected as shown below:

<u>Column 12,</u>
Line 36, "Cyclopropylpheryl" should read -- Cyclopropylphenyl --.
Line 39, delete "an animal or" and replace with -- a --.

Signed and Sealed this

Ninth Day of July, 2002

*Attest:*

*Attesting Officer*

JAMES E. ROGAN
*Director of the United States Patent and Trademark Office*